United States Patent [19]

Fauran et al.

[11] 4,041,072
[45] Aug. 9, 1977

[54] ACETAMIDOXIME COMPOUNDS

[75] Inventors: Claude P. Fauran, Paris; Guy R. Bourgery, Colombes; Claude J. Gouret, Meudon, all of France

[73] Assignee: Delalande S. A., Courbevoie, France

[21] Appl. No.: 668,061

[22] Filed: Mar. 18, 1976

[30] Foreign Application Priority Data

Mar. 25, 1975 France .................................. 75.09263
Feb. 24, 1976 France .................................. 76.05098

[51] Int. Cl.² .................. C07C 103/28; C07C 103/76; C07C 103/365; A61K 31/165
[52] U.S. Cl. .......................... 260/558 A; 260/559 A; 260/562 N; 424/324
[58] Field of Search .......... 260/558 A, 559 A, 562 N

[56] References Cited

U.S. PATENT DOCUMENTS

| | | | |
|---|---|---|---|
| 3,414,614 | 12/1968 | Julia | 260/558 A |
| 3,560,555 | 2/1971 | Fucho | 260/566 AC X |
| 3,624,151 | 11/1971 | Gutman | 260/562 N X |
| 3,636,111 | 1/1972 | Karten | 260/566 AC |
| 3,766,270 | 10/1973 | Hiller et al. | 260/562 N |
| 3,819,700 | 6/1974 | Bellina | 260/562 N X |
| 3,867,447 | 2/1975 | Cherkofsky | 260/566 R X |
| 3,872,169 | 3/1975 | Bellina | 260/558 A |
| B 533,652 | 3/1976 | Cherkofsky | 260/558 A X |

Primary Examiner—Daniel E. Wyman
Assistant Examiner—Thomas A. Waltz
Attorney, Agent, or Firm—Blanchard, Flynn, Thiel, Boutell & Tanis

[57] ABSTRACT

Compounds having the formula

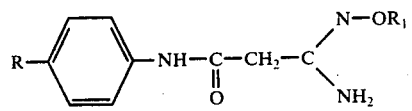

wherein R is hydrogen, or chlorine, or alkyl having one to 4 carbons, or alkoxy having one to 3 carbons, and $R_1$ is hydrogen, or

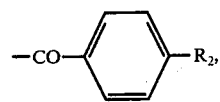

or $-CONH-R_3$, wherein $R_2$ is hydrogen, or chlorine, or nitro, or alkoxy having no more than 3 carbons, or trifluoromethyl, and $R_3$ is alkyl having one to 4 carbons, or cycloalkyl having no more than 6 carbons, or phenyl.

The compounds are prepared by reacting R-substituted cyano-2 acetanilides with hydroxylamine to obtain compounds in which $R_1$ is hydrogen, and then reacting with acid chlorides containing $R_2$ or isocyanates containing $R_3$. The compounds possess psychtropic properties.

19 Claims, No Drawings

ACETAMIDOXIME COMPOUNDS

The present invention relates to novel acetamidoximes, their method of preparation and their application in therapeutics, particularly as a psychotrope.

More particularly, the present invention has as object derivatives having the general formula (I):

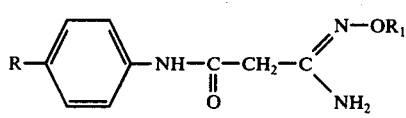
(I)

in which:
R represents a hydrogen atom, a chlorine atom, an alkyl group having from 1 to 4 carbon atoms or an alkoxy group having from 1 to 3 carbon atoms, and $R_1$ represents:
either a hydrogen atom,
or a benzoyl group of formula:

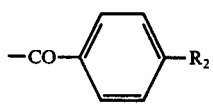

in which
$R_2$ designates a hydrogen atom, a chlorine atom, a nitro group, an alkoxy group having no more than 3 carbon atoms, or a trifluoromethyl group, or a carbamoyl group of formula:

where
$R_3$ represents an alkyl group having from 1 to 4 carbon atoms, a cycloalkyl group having no more than 6 carbon atoms or a phenyl ring.

The method of the invention consists in reacting a cyano - 2 acetanilide having the general formula (II):

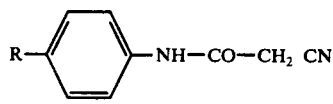
(II)

in which R has the same significance as in formula (I) with hydroxylamine; then possibly reacting on the products thus obtained a compound chosen from:
the chlorides of acids of formula (III)

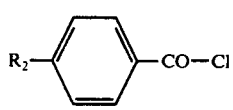
(III)

in which $R_2$ has the same significance as in formula (I) or
the isocyanates of formula (IV)

$$R_3 - N = C = O \quad (IV)$$

in which $R_3$ has the same significance as in formula (I)

The compounds of formula (II), which are all known, are obtained by action of ethyl cyanacetate of formula (V):

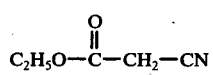
(V)

on an aniline of formula (VI)

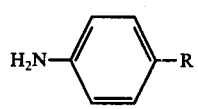
(VI)

in which R has the same significance as in formula (I).

The following preparations are given as examples to illustrate the invention.

EXAMPLE 1

Anilinocarbamoyl - 2 acetamidoxime

Code number 76.0041

To a solution of 11.5 g of sodium in 300 cm3 of methanol is added a solution of 34.8 g (0.5 mole) of hydroxylamine hydrochloride in 100 ml of methanol. They are left in contact for 15 minutes, then the sodium chloride is filtered. To the filtrate is added 64 g (0.4 mole) of cyano - 2 acetanilide, it is brought to reflux for 8 hours, then the solvent is evaporated and the residue obtained is recrystallized in 600 ml of 96° ethanol.

melting point: 175° C
yield: 52 %
empirical formula: $C_9 H_{11} N_3 O_2$
elementary analysis

|  | C | H | N |
|---|---|---|---|
| Calculated (%) | 55.95 | 5.74 | 21.75 |
| Found (%) | 55.80 | 5.87 | 21.70 |

EXAMPLE 2 p-anisidocarbamoyl - 2 acetamidoxime

Code number 74.0285

To a solution of 62.6 g of sodium in 1.700 ml of methanol is added a solution of 189 g (2.72 moles) of hydroxylamine hydrochloride in 550 ml of methanol. They are left in contact for 15 minutes and then filtered. To the filtrate is added 417 g (2.18 moles) of cyano - 2 methoxy - 4' acetanilide, it is brought to reflux for 7 hours, filtered and the product obtained is recrystallized in ethanol.

melting point: 191° C
yield: 70 %
empirical formula: $C_{10} H_{13} N_3 O_3$
elementary analysis

|  | C | H | N |
|---|---|---|---|
| Calculated (%) | 53.80 | 5.87 | 18.83 |
| Found (%) | 53.78 | 5.84 | 19.09 |

EXAMPLE 3 p - anisidocarbamoyl -2 O- anilinocarbamoyl acetamidoxime

Code number 74.0431

To a solution of 66.9 g (0.3 mole) of para anisido - carbamoyl - 2 acetamidoxime prepared in example 2 in 300 ml of chloroform is added a solution of 35.7 (0.3 mole) of phenyl isocyanate in 300 ml of chloroform. They are left for 2 hours at 20° C, brought to reflux for 3 hours, then the solvent is evaporated. The residue is recrystallized in 1.000 ml of 96° ethanol.

melting point: 187° C
yield: 78 %
empirical formula: $C_{17}H_{18}N_4O_4$
elementary analysis

|  | C | H | N |
|---|---|---|---|
| Calculated (%) | 59.64 | 5.30 | 16.37 |
| Found (%) | 59.93 | 5.31 | 16.18 |

EXAMPLE 4 p-anisido - carbamoyl -2 O- benzoyl acetamidoxime

Code number 76.0086

To a solution of 15 g (0.0675 mole) of para anisido - carbamoyl - 2 acetamidoxime prepared in example 2 and 6.8 g (0.0675 mole) of triethylamine in 100 ml of benzene is added a solution of 9.5 g (0.0675 mole) of benzoyl chloride in 100 ml of benzene and they are brought to reflux for 3.5 hours. Then they are filtered, the precipate is washed in 500 ml of hot water, and recrystallized in 400 ml of 96° ethanol.

melting point: 190° C
yield: 67%
empirical formula: $C_{17}H_{17}N_3O_4$
elementary analysis

|  | C | H | N |
|---|---|---|---|
| Calculated (%) | 62.37 | 5.24 | 12.84 |
| Found (%) | 62.18 | 5.32 | 13.10 |

The acetamidoximes of formula (I) shown in the following table I were prepared according to a procedure similar to those described above.

Table I

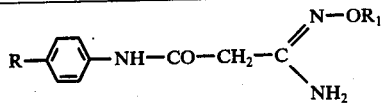

| Code Number | R | $R_1$ | Empirical formula | Molecular weight | Melting point (° C) | Rendement (%) |
|---|---|---|---|---|---|---|
| 74.0016 | Cl | H | $C_9H_{10}ClN_3O_2$ | 227.65 | 171 | 29 |
| 76.0090 | $CH_3$ | H | $C_{10}H_{13}N_2O_2$ | 207.2 | 180 | 54 |
| 74.0358 | $CH_3O$ | CO—NH—$CH_3$ | $C_{12}H_{16}N_4O_4$ | 280.28 | 155 | 58 |
| 74.0449 | $CH_3O$ | CO—NH—$C_3H_{7n}$ | $C_{14}H_{20}N_4O_4$ | 308.33 | 150 | 38 |
| 74.0315 | $CH_3O$ | CO—NH—⟨cyclohexyl⟩ | $C_{17}H_{24}N_4O_4$ | 348.39 | 180 | 42 |
| 76.0094 | $CH_3$ | CO—NH—⟨phenyl⟩ | $C_{17}H_{18}N_4O_3$ | 326.35 | 205 | 60 |
| 76.0043 | H | CO—NH—$CH_3$ | $C_{11}H_{14}N_4O_3$ | 250.25 | 150 | 47 |
| 74.0337 | $CH_3O$ | —CO—⟨C₆H₄⟩—$NO_2$ | $C_{17}H_{16}N_4O_6$ | 372.33 | 224 | 81 |
| 74.0368 | $CH_3O$ | —CO—⟨C₆H₄⟩—Cl | $C_{17}H_{16}ClN_3O_4$ | 361.78 | 218 | 60 |
| 76.0093 | $CH_3$ | —CO—⟨phenyl⟩ | $C_{17}H_{17}N_3O_3$ | 311.33 | 188 | 77 |
| 76.0087 | $CH_3O$ | —CO—⟨C₆H₄⟩—$OCH_3$ | $C_{18}H_{19}N_3O_5$ | 357.36 | 200 | 70 |
| 76.0112 | $CH_3O$ | —CO—⟨C₆H₄⟩—$CF_3$ | $C_{18}H_{16}F_3N_3O_4$ | 395.33 | 230 | 59 |

| Code Number | ELEMENTARY ANALYSIS Calculated (%) | | | Found (%) | | |
|---|---|---|---|---|---|---|
|  | C | H | N | C | H | N |
| 74.0016 | 47.48 | 4.43 | 18.46 | 47.26 | 4.39 | 18.29 |
| 76.0090 | 57.96 | 6.32 | 20.28 | 57.99 | 6.24 | 20.34 |
| 74.0358 | 51.42 | 5.75 | 19.99 | 51.51 | 5.60 | 19.85 |
| 74.0449 | 54.53 | 6.54 | 18.17 | 54.62 | 6.54 | 17.96 |
| 74.0315 | 58.60 | 6.94 | 16.08 | 58.72 | 6.89 | 15.99 |
| 76.0094 | 62.56 | 5.56 | 17.17 | 62.34 | 5.72 | 16.96 |
| 76.0043 | 52.79 | 5.64 | 22.39 | 52.77 | 5.58 | 22.38 |
| 74.0337 | 54.84 | 4.33 | 15.05 | 54.90 | 4.30 | 14.98 |
| 74.0368 | 56.44 | 4.46 | 11.62 | 56.36 | 4.65 | 11.83 |
| 76.0093 | 65.58 | 5.50 | 13.50 | 65.63 | 5.75 | 13.21 |
| 76.0087 | 60.49 | 5.36 | 11.76 | 60.37 | 5.42 | 11.96 |
| 76.0112 | 54.68 | 7.61 | 10.63 | 54.47 | 7.61 | 10.95 |

The compounds of formula (I) were studied on laboratory animals and showed psychotropic properties.

In fact, administered by mouth as a preventive to a mouse, they are able to oppose ptosis caused by intravenous injection of reserpine.

Following table II gives the 50 effective dose for some compounds of formula (I) and for comparison the 50 effective dose of imipramine, a compound well known for its psychotropic properties.

Table II

| Code number of compound tested | Effective dose 50 (mg/kg/p.o) |
| --- | --- |
| 74.0285 | 10.0 |
| 74.0337 | 1.0 |
| 74.0358 | 4.5 |
| 74.0431 | 1.0 |
| 74.0449 | 3.0 |
| 76.0041 | ·5.5 |
| 76.0086 | 5.5 |
| Imipramine | 9.0 |

Furthermore, the compounds of formula (I) are not very toxic since no case of mortality was observed after oral administration to a mouse of 2000 mg/kg of these compounds. The result is that, for the compounds of the invention, the difference between the above-cited pharmacologically active doses and lethal doses is sufficient to allow their use in therapeutics.

It is to be noted that the 50 lethal dose of imipramine is, under the same conditions, equal to 550 mg/kg/p.o.

From the preceding it is clear that the compounds of the invention have a therapeutical index between the values (>200) and (>2000) whereas the therapeutical index of imipramine is only 60.

This shows the undeniable superiority of the compounds of the invention over imipramine.

The compounds of formula (I) are indicated for troubles of the psychism.

They should be administered orally in the form of tablets, pills or gelules containing 50 to 300 mg of active constituent (1 to 6 per day), in solution form containing 0.5 to 5 % of active constituent (20 to 60 drops — 1 to 3 times per day), or parenterally in the form of injectable phials containing 10 to 150 mg/kg of active constituent (1 to 3 per day).

What we claim is:

1. A compound having the formula

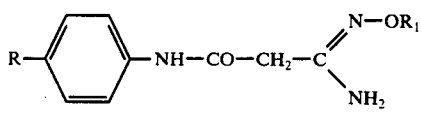

wherein

R is hydrogen, chloro, alkyl having one to 4 carbons or alkoxy having one to 3 carbons, R₁ is hydrogen,

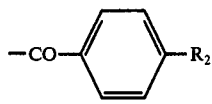

wherein

R₂ is hydrogen, chloro, nitro, alkoxy having one to 3 carbons or —CF₃ or —CO—NH—R₃ wherein R₃ is alkyl having one to 4 carbons, cycloalkyl having no more than 6 carbons, or phenyl.

2. A compound as claimed in claim 1, in which R is hydrogen and R₁ is hydrogen.

3. A compound as claimed in claim 1, in which R is chloro and R₁ is hydrogen.

4. A compound as claimed in claim 1, in which R is methyl and R₁ is hydrogen, anilinocarbamoyl or benzoyl.

5. A compound as claimed in claim 1, in which R is methoxy and R₁ is hydrogen, anilinocarbamoyl, N-methyl carbamoyl, N-n-propyl carbamoyl, N-cyclohexyl carbamoyl, p-nitrobenzoyl, p-chlorobenzoyl, benzoyl, p-methoxybenzoyl or p-CF₃ benzoyl.

6. A compound as claimed in claim 1 in which R₁ is hydrogen.

7. A compound as claimed in claim 1 in which R₁ is

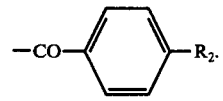

8. A compound as claimed in claim 1 in which R₁ is —CO—NH—R₃.

9. A compound as claimed in claim 1 in which R is hydrogen and R₁ is —CO—NH—CH₃.

10. A compound as claimed in claim 1 in which R is methoxy and R₁ is hydrogen.

11. A compound as claimed in claim 1 in which R is methoxy and R₁ is anilinocarbamoyl.

12. A compound as claimed in claim 1 in which R is methoxy and R₁ is N-methyl-carbamoyl.

13. A compound as claimed in claim 1 in which R is methoxy and R₁ is N-n-propyl carbamoyl.

14. A compound as claimed in claim 1 in which R is methoxy and R₁ is N-cyclohexyl carbamoyl.

15. A compound as claimed in claim 1 in which R is methoxy and R₁ is p-nitrobenzoyl.

16. A compound as claimed in claim 1 in which R is methoxy and R₁ is p-chlorobenzoyl.

17. A compound as claimed in claim 1 in which R is methoxy and R₁ is benzoyl.

18. A compound as claimed in claim 1 in which R is methoxy and R₁ is p-methoxybenzoyl.

19. A compound as claimed in claim 1 in which R is methoxy and R₁ is p-CF₃ benzoyl.

* * * * *